United States Patent [19]
Gamelin

[11] Patent Number: 5,410,983
[45] Date of Patent: May 2, 1995

[54] DEVICE AND INSTALLATION FOR CRYSTAL GROWTH HAVING OBSERVATION MEANS

[75] Inventor: Christian Gamelin, Saint Aubin de Medco, France

[73] Assignee: Societe Anonyme dite: Aerospatiale Societe Nationale, Paris, France

[21] Appl. No.: 693,319

[22] Filed: Apr. 29, 1991

[30] Foreign Application Priority Data

May 31, 1990 [FR] France .................. 90 06792

[51] Int. Cl.⁶ .............................................. C30B 35/00
[52] U.S. Cl. ................................................. 117/202
[58] Field of Search .............. 156/600, 601, DIG. 62, 156/DIG. 89, DIG. 93; 422/245, 248

[56] References Cited
U.S. PATENT DOCUMENTS

| | | | |
|---|---|---|---|
| 4,508,970 | 4/1985 | Ackerman | 156/601 |
| 4,886,646 | 12/1989 | Carter et al. | 156/600 |
| 4,919,899 | 4/1990 | Hermann et al. | 156/601 |
| 4,969,745 | 11/1990 | Ibe | 156/601 |

FOREIGN PATENT DOCUMENTS

| | | |
|---|---|---|
| 0265319 | 4/1988 | European Pat. Off. |
| 0289200 | 11/1988 | European Pat. Off. |
| 0129690 | 2/1978 | Germany |
| 3904858 | 9/1989 | Germany |

OTHER PUBLICATIONS

*Journal of Crystal Growth*, vol. 73, No. 2, Nov., 1985, pp. 364–368, R. F. Karlicek et al., "Remote Optical Monitoring of Reactants in a Vapor Phase Epitaxial Reactor."

Primary Examiner—R. Bruce Breneman
Assistant Examiner—Felisa Garrett
Attorney, Agent, or Firm—Marshall, O'Toole, Gerstein, Murray & Borun

[57] ABSTRACT

A crystal growth device is disclosed comprising a crucible in the cavity of which a crystallization reaction may take place to make possible the automatic and accurate observation of crystallization in miniaturized installation.

12 Claims, 2 Drawing Sheets

DEVICE AND INSTALLATION FOR CRYSTAL GROWTH HAVING OBSERVATION MEANS

BACKGROUND OF THE INVENTION

The present invention relates to a crystal growth device and an installation having means for observing the crystallization.

One of the methods of studying macromolecular substances consists in forming crystals of said substances and subjecting said crystals to examination, particularly spectrography. To form such crystals, diffusion methods are used, possibly through a porous diffusion wall. For this, a crucible filled with a liquid mixture of the macromolecular substance to be studied and a precipitating agent in a concentration insufficient for acting, is placed in an enclosure, then such a precipitating agent is introduced into said enclosure for causing crystallization by reducing the concentration of substance (liquid phase) or increasing it (vapor phase) or with constant concentration (dialysis).

By diffusion, the concentration of the mixture of precipitating agent and macromolecular substance contained in the crucible tends to align itself on that of the precipitating agent contained in the enclosure. Consequently, by varying the concentration of the precipitating agent, the crystallization of said macromolecular substance can be adjusted.

Generally, the crucible and the enclosure are at least partially transparent, so that an operator may visually follow the development of crystallization. However, such visual observation cannot be precise. In addition, it becomes difficult, if not impossible, if said crucible is of a small size and/or if a plurality of experiments are conducted simultaneously using an installation combining a plurality of crucibles, close together.

Furthermore, the crystals obtained in land-based laboratories using such diffusion techniques are not perfect, not only from the quality but also from the size point of view, particularly because of convection phenomena due to gravity.

To overcome this drawback, it is advantageous to be able to use such diffusion techniques on board space vessels, for then the conditions of weightlessness eliminate such convection phenomena.

It goes without saying that such use in space of crystal growth methods involves the miniaturization of the crucibles and of the installations grouping them together. It is then necessary to provide an automatic system for observing the crystal growth reactions.

SUMMARY OF THE INVENTION

The object of the present invention is then to make possible the automatic and accurate observation of crystallization reactions in miniaturized installations, particularly, but not exclusively, on board space vehicles.

For this, according to the invention, a crystal growth device comprising a crucible in the cavity of which a crystallization reaction may take place is remarkable in that it comprises:

light generating means disposed outside said cavity, on the same side as the base of said crucible;

light detection means disposed outside said cavity also on the same side as the base of said crucible;

first light transmission means disposed between said light generating means and the cavity of said crucible for introducing into said cavity a first light beam parallel to a first direction; and second light transmission means disposed between the cavity of said crucible and said light detection means for taking from said cavity a second light beam parallel to a second direction, which is transverse to said first direction.

Thus, with the present invention, since the light generating means and the light detection means, associated with each crucible, are disposed thereunder, crystal growth installations may be formed in which a plurality of crucibles are disposed coplanarly side by side, with a length and width dimension as small as possible.

In addition, the observation of the crystallization reaction is precise. In fact, because of the arrangement of said first and second beams, said light detection means only collect the light diffused and/or diffracted by the crystals contained in the cavity of the crucible, i.e. at all times, the output signal of said light detection means is representative of the amount and/or of the size of said crystals and so of the state of the crystallization reaction. It will be further noted that with such an arrangement the light detection means do not risk being blinded by said light generating means, since said first light beam is not directed towards said light detection means.

Advantageously, in the device of the invention, said crucible, said light generating means, said light detection means said first light transmission means and said second light transmission means are fastened together to form a crystal growth unit.

Preferably, said reaction unit comprises a geometrical axis orthogonal to the base of said crucible and:

said light generating means are off-centered with respect to said axis;

said first light transmission means comprise at least one light duct off-centered with respect to said axis and deflection means for deflecting said first light beam in the direction of the cavity of said crucible;

said light detection means are centered on said axis; and said second light transmission means are formed at least partially by the base of said crucible which, for this, is transparent for said second light beam.

It is then advantageous:

for said light generating means to comprise a plurality of light sources distributed about said axis; and for said first light transmission means to comprise a plurality of light ducts, each of which is associated with a light source.

Said deflection means may be formed in this case by a conical mirror, concentric with the geometrical axis of said crystal growth unit. This conical mirror may be formed by a metallized face formed in said crucible.

Similarly, the light duct or ducts may be formed by cylindrical channels with metallized wall formed in said crucible. Such channels are advantageously parallel to the axis of said crystal growth unit.

In order to concentrate, in said light ducts, the light emitted by said light generating means, an optical system is preferably provided between said light generating means and the light duct or ducts.

Similarly, an optical system is provided between the base of said crucible and said light detection means.

Said light generating means and said light detection means may advantageously be of electric type. For example, the or each source of said light generating means is formed by an LED, whereas said light detection means are formed by a photodiode, a photovoltaic element, a photo transistor or a pyroelectric detector. In this case, said crystal growth device comprises in addition control means for controlling said light generating means and/or said light detection means and for delivering an electric signal representative of the light intensity of said second light beam. The invention also relates to a crystal growth installation comprising a plurality of devices, such as that specified above. In accordance with the invention, such an installation is remarkable:
in that each device comprises:
  electric light generating means disposed outside said cavity, on the same side as the base of said crucible;
  electric light detection means disposed outside said cavity, also on the same side as the base of said crucible;
  first light transmission means disposed between said light generating means and the cavity of said crucible for introducing into said cavity a first light beam parallel to a first direction; and
  second light transmission means disposed between the cavity of said crucible and said light detection means for taking from said cavity a second light beam parallel to a second direction, which is transverse to said first direction;
and in that control means are provided for controlling said light generating means and said light detection means and for delivering electric signals representative respectively of the light intensity of each of said second light beams.

BRIEF DESCRIPTION OF THE DRAWINGS

The figures of the accompanying drawings will better show how the invention may be put into practice. In these figures, identical references designate similar elements.

DESCRIPTION OF THE PREFERRED EMBODIMENTS

Figure 1:
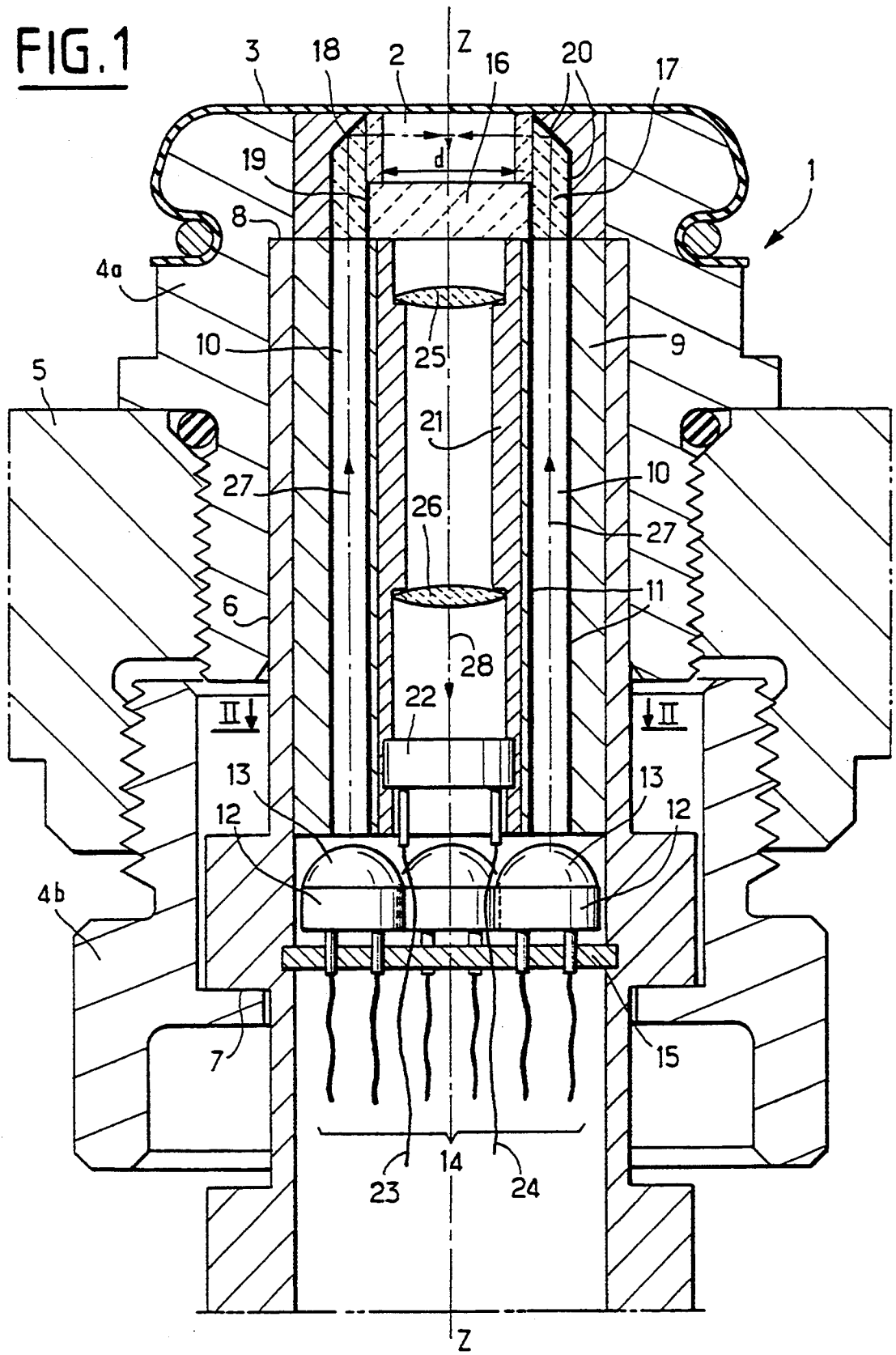
FIG. 1 is an enlarged axial sectional view of a crystal growth device according to the present invention.

The crystal growth device 1, according to the present invention and shown in FIG. 1, comprises a crucible with geometrical axis Z-Z having a crystal growth cavity 2.

The process of crystal growth inside cavity 2 may be conducted as described in the French patent FR-A-2 604 917. In this case, the crystal growth device 1 replaces the crucible 4 and the observation device 32 described in this prior French patent. However, the device 1 according to the present invention may also serve for implementing the known crystal growth process described above. In the present FIG. 1, the enclosure for introducing the precipitating agent has not been shown. Only a diffusion membrane 3, closing cavity 2, has been shown.

The crucible shown in FIG. 1 has two parts 4a and 4b, for fixing said crucible to a support 5.

The two crucible portions 4a and 4b are cylindrical and hollow and coaxial with the axis Z-Z. The cavity 5 is itself cylindrical and coaxial with the axis Z-Z. Its diameter d may be of the order of 5 mm.

Inside the crucible portions 4a and 4b is mounted a sleeve 6 blocked between two shoulders 7 and 8, respectively provided on said crucible portions.

Figure 2:
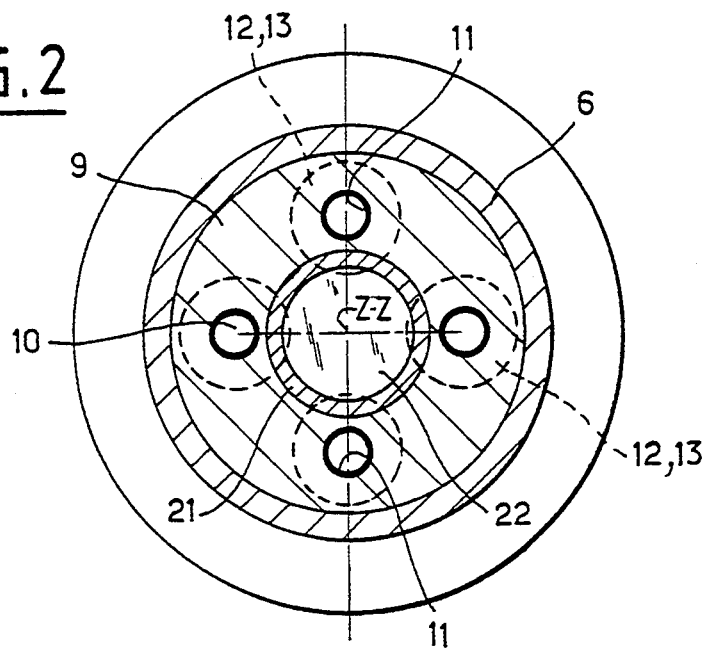
FIG. 2 is a section through line II—II of FIG. 1.

In addition, a cylindrical axial hollow body 9 (see also FIG. 2) is disposed and held inside sleeve 6. The cylindrical body 9 is formed with peripheral cylindrical channels 10, parallel to the axis Z-Z. The wall of each cylindrical channel 10 is coated with a reflecting metallization 11. The cylindrical channels 10 are for example four in number and are distributed evenly angularly about the axis Z-Z.

With each cylindrical channel 10 is associated an LED 12, itself associated with a focussing optical system 13. The LEDs 12 are connected to electric conductors 14. They are carried by a support 15, itself supported by sleeve 6, and each of them is situated opposite a channel 10, at the base thereof.

The cavity 2 of crucible 4a, 4b is defined by a bottom or base 16, which is transparent and rests on the central portion of body 9, and by a peripheral ring 17, also transparent, comprising a conical end chamfer 18. The cylindrical outer surface of base 16 carries a reflecting metallization 19. Similarly, the outer surface of ring 17 and the conical chamfer 18 carry a reflecting metallization 20. The metallizations 19 and 20 extend the metallizations 11 of channels 10.

Inside body 9 is disposed a sleeve 21 which holds in position, on its base side, a photodiode 22 connected to conductors 23 and 24. In sleeve 21, between the base 16 of cavity 2 and the photodiode 22, is arranged an optical focussing system, formed for example of two convergent lenses 25 and 26.

Thus, when the LEDs 12 are activated via conductors 14, they emit light which, focussed by lenses 13, penetrates into channels 10. By total reflection from the metallized wall 11 of said channels, this light is propagated therein in the form of beams, only the axes 27 of which have been shown in FIG. 1. These beams continue their propagation because of the metallizations 19 and 20 of the external cylindrical surfaces of base 16 and of the peripheral ring 17. However, because of the metallization 20 of the conical chamfer 18, these beams are deflected, for example through 90°, in the direction of cavity 2. If this cavity 2 contains crystals, they are illuminated by said deflected beams so that they generate diffused light (if these crystals are small) and/or diffracted light (if these crystals are large).

A portion of this diffused and/or diffracted light passes through the transparent base 16 of cavity 2 and the optical system forms a beam 28 (symbolized in FIG. 1 by its axis merging with the axis Z-Z), which is received by the photodiode 22. The latter, fed by its conductor 23, then delivers an electric output signal over conductor 24. This output signal of photodiode 22, being representative of the light intensity of the diffused and/or diffracted beam 28, which itself is representative of the state of formation of crystals inside cavity 2, is therefore representative of this state.

Thus, with the invention, by following the evolution of the output signal of photodiode 22, the state of crystal formation inside cavity 2 may be known at all times.

Figure 3:
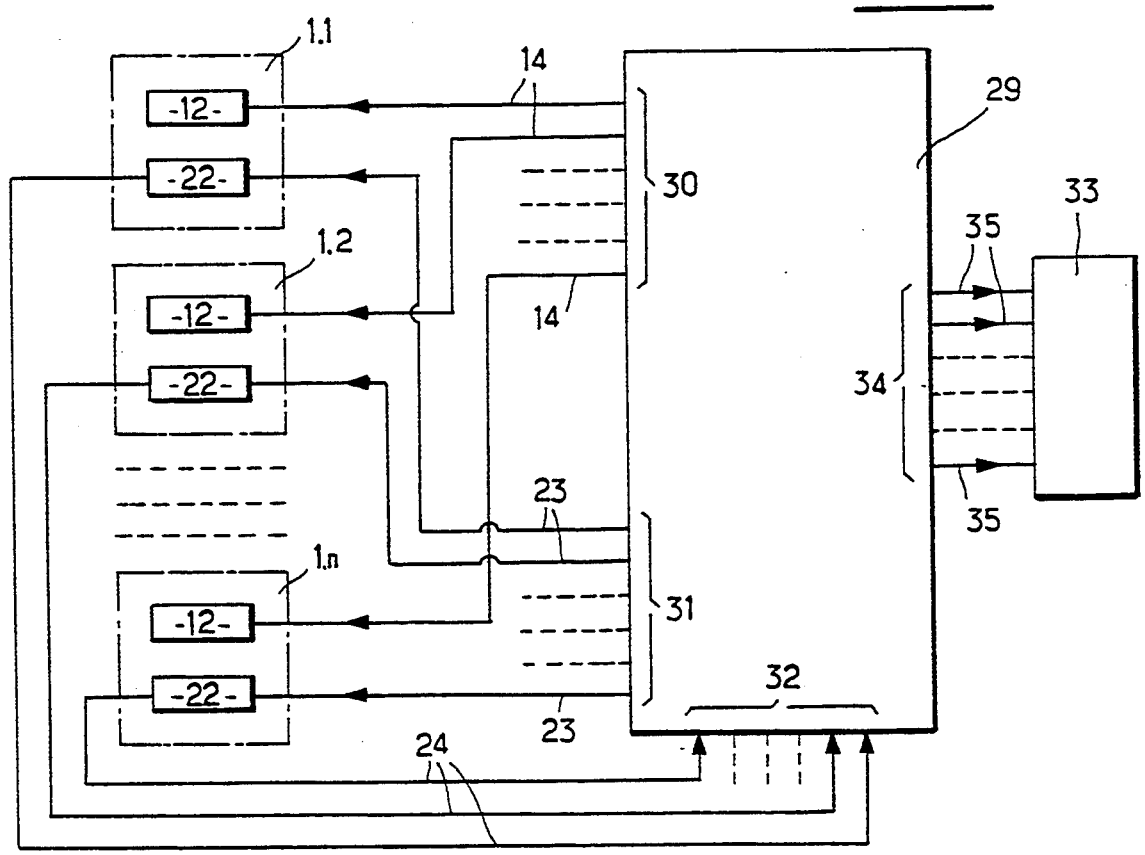
FIG. 3 shows the block diagram of an installation according to the present invention comprising a plurality of the devices shown in FIGS. 1 and 2.

In FIG. 3, a plurality of devices 1 have been shown schematically bearing respectively the references 1.1, 1.2, ... 1.n and controlled by a microprocessor control device 29. The latter comprises a first group of outputs 30 which, via conductors 14, are capable of controlling the LEDs of all the devices 1.1 to 1.n. This control device 29 in addition comprises a second group of outputs 31 by which, via conductors 23, it controls the supply to the photodiodes 22. Furthermore, the control device 29 comprises a group of inputs 32 which, via conductors 24, receive the output signals of said photodiodes 22.

Device 29 is capable of controlling the different devices 1.1 to 1.n and transmitting to a display device 33, via a group of outputs 34 and connections 35, the instantaneous state of the crystallization reaction in cavity 2 of each of said devices 1.1 to 1.n.

It will be noted that even in the absence of crystallization reaction in the cavity 2, the corresponding detector 22 receives stray light. It is then indispensable to measure this stray light so that device 29 takes it into account and delivers relative measurements.

What is claimed is:

1. Crystal growth device comprising a crucible having a base which defines in part a cavity in which a crystallization reaction may take place, comprising:
   light generating means disposed outside said cavity, on the same side as the base of said crucible;
   light detection means disposed outside said cavity, also on the same side as the base of said crucible;
   first light transmission means disposed between said light generating means and the cavity of said crucible for introducing into said cavity a first light beam parallel to a first direction; and
   second light transmission means disposed between the cavity of said crucible and said light detection means for taking from said cavity a second light beam parallel to a second direction, which is transverse to said first direction, said second beam being light from said first beam which is diffused or diffracted by crystals present in said cavity.

2. The crystal growth device as claimed in claim 1, wherein said crucible, said light generating means, said light detection means said first light transmission means and said second light transmission means are fastened together to form a crystal growth unit.

3. The crystal growth device as claimed in claim 2, wherein:
   said crystal growth unit comprises a geometrical axis orthogonal to the base of said crucibles;
   said light generating means are off-centered with respect to said axis;
   said first light transmission means comprise at least one light duct off-centered with respect to said axis and deflection means for deflecting said first light beam in the direction of the cavity of said crucible;
   said light detection means are centered on said axis; and
   said second light transmission means are formed at least partially by the base of said crucible which, for this, is transparent for said second light beam.

4. The crystal growth device as claimed in claim 3, wherein:
   said light generating means comprise a plurality of light sources distributed about said axis; and
   said first light transmission means comprise a plurality of light ducts, each of which is associated with a light source.

5. The crystal growth device as claimed in claim 4, wherein said deflection means are formed by a conical mirror, concentric with said axis.

6. The crystal growth device as claimed in claim 5, wherein said conical mirror is formed by a metallized face.

7. The crystal growth device as claimed in claim 3, wherein the light duct or ducts are formed by cylindrical channels with metallized wall.

8. The crystal growth device as claimed in claim 3, wherein said light duct or ducts are parallel to the axis of said crystal growth unit.

9. The crystal growth device as claimed in claim 3, wherein said first light transmission means comprise an optical system between said light generating means and said light duct or ducts.

10. The crystal growth device as claimed in claim 3, wherein said second light transmission means comprise an optical system between the base of said crucible and said light detection means.

11. The crystal growth device as claimed in claim 1, wherein said light generating means and said light detection means are electric and control means are provided for controlling said light generating means and said light detection means and for delivering an electric signal representative of the light intensity of said second light beam.

12. The crystal growth installation comprising a plurality of devices each of which comprises a crucible in the cavity of which a crystallization reaction may take place, wherein each device comprises:
   electric light generating means disposed outside said cavity, on the same side as the base of said crucible;
   electric light detection means disposed outside said cavity, also on the same side as the base of said crucible;
   first light transmission means disposed between said light generating means and the cavity of said crucible for introducing into said cavity a first light beam parallel to a first direction; and
   second light transmission means disposed between the cavity of said crucible and said light detection means for taking from said cavity a second light beam parallel to a second direction, which is transverse to said first direction;
and control means are provided for controlling said light generating means and said light detection means and for delivering electric signals representative respectively of the light intensity of each of said second light beams.

* * * * *

UNITED STATES PATENT AND TRADEMARK OFFICE
CERTIFICATE OF CORRECTION

PATENT NO.    : 5,410,983
DATED         : May 2, 1995
INVENTOR(S)   : Christian Gamelin It is certified that error appears in the above-identified patent and that said Letters Patent is hereby corrected as shown below:

```
On the title page, item [73] Assignee:  "Societe Anonyme dite:  Aerospatiale
Societe Nationale" should be --Aerospatiale Societe Nationale Industrielle--
```

Signed and Sealed this

Twenty-first Day of November, 1995

*Attest:*

BRUCE LEHMAN

*Attesting Officer*    *Commissioner of Patents and Trademarks*